United States Patent [19]

Newman

[11] Patent Number: 5,586,563

[45] Date of Patent: Dec. 24, 1996

[54] METHOD FOR MAKING A SURGICAL DRAPE

[75] Inventor: Charles L. Newman, Stillwater, Minn.

[73] Assignee: Minnesota Mining and Manufacturing Company, St. Paul, Minn.

[21] Appl. No.: 546,587

[22] Filed: Oct. 23, 1995

[51] Int. Cl.[6] .................................................. A61B 19/00
[52] U.S. Cl. ......................................... 128/849; 128/853
[58] Field of Search ...................................... 128/849–856

[56]  References Cited

U.S. PATENT DOCUMENTS

| Re. 26,759 | 1/1970 | Melges | 128/132 |
|---|---|---|---|
| 2,593,121 | 4/1952 | Djorup | 2/114 |
| 2,715,902 | 8/1955 | Shaffer et al. | 128/132 |
| 3,030,957 | 4/1962 | Melges | 128/292 |
| 3,809,077 | 5/1974 | Hansen | 128/132 D |
| 3,856,005 | 12/1974 | Sislian | 128/132 D |
| 3,856,006 | 12/1974 | Krzewinski | 128/132 D |
| 3,862,632 | 1/1975 | Hinsch | 128/132 D |
| 4,040,418 | 8/1977 | Collins | 128/852 |
| 4,522,203 | 6/1985 | Mays | 128/132 D |
| 4,539,256 | 9/1985 | Shipman | 428/315.5 |
| 4,574,796 | 3/1986 | Lundstrom | 128/855 |
| 4,586,498 | 5/1986 | Morris | 128/132 D |
| 4,889,136 | 12/1989 | Hanssen | 128/855 |
| 4,976,274 | 12/1990 | Hanssen | 128/849 |
| 5,260,360 | 11/1993 | Mrozinski et al. | 524/95 |
| 5,452,729 | 9/1995 | Bergsbaken et al. | 128/849 |

Primary Examiner—Michael A. Brown
Attorney, Agent, or Firm—Gary L. Griswold; Walter N. Kirn; Jennie G. Boeder

[57] ABSTRACT

A surgical drape and a method of simultaneously forming a drape blank a surgical drape in a single operation having both a screen portion and a fitted portion. A first continuous web forming a body portion of a surgical drape is advanced along a first longitudinal axis to a cutting and bonding location. A second web having first and second long edges generally parallel to a second longitudinal axis is located so that the first long edge of the second web is adjacent to the cutting and bonding location. A curvilinear seam is formed between the first and second webs along a path extending into the second web. The path generally originates and terminates at the intersection of the first long side of the second web and the first and second long edges of the first continuous web, respectively. The seam is cut generally along the path so that a first portion of the second web forms a fitted portion with the body portion of a first surgical drape in the series of surgical drapes. A second portion of the second web forms a screen portion attached to the body portion of a second surgical drape in the series of surgical drapes.

23 Claims, 4 Drawing Sheets

METHOD FOR MAKING A SURGICAL DRAPE

FIELD OF THE INVENTION

The present invention relates to a surgical drape and a method for making a series of surgical drapes, each drape having an elongated body portion for covering a patient with an anesthetist's screen attached at one end and a fitted portion attached at the opposite end. More particularly, the present invention relates to a method for simultaneously forming in a single operation a drape blank having an anesthetist's screen at one end and a fitted portion at the other end.

BACKGROUND OF THE INVENTION

Surgical drapes are used to perform the dual function of covering the patient and creating a barrier between the anesthetist and the surgical area. The screen portion of the surgical drape is typically attached to, and supported by, an anesthetist's arch or stand which extends transversely across and above the operating table. The portion of the surgical drape covering the patient is intended to hang down along the sides and foot portion of the operating table, while the screen or drape portion ideally extends beyond the side edges of the operating table.

The transition between the body portion of the surgical drape and the screen or drape portion must be configured to accommodate surgery performed proximate the screen or drape, such as operations performed on the upper chest region. One attempt to construct a surgical drape with a smooth transition between the screen and body portion of the drape is disclosed in U.S. Pat. No. 4,889,136 issued to Hanssen on Dec. 26, 1989. As illustrated in FIG. 3 of Hanssen, two material webs, A' and B', are advanced to two clipping and punching devices 12 and 13. The clipping device 12 forms a cut 14 through the material web B' in a direction perpendicular to the feeding direction. The clipping device 13 is constructed to cut out a piece 15 in the shape of an isosceles trapezoid with cut lines $15_1$–$15_4$ from both of the webs A' and B'. Consequently, the piece 15 in both the webs A' and B' constitutes waste. In an alternate embodiment, the clipping device 13 is arranged to cut the piece 15 solely along the cut lines $15_2$–$15_4$, so that only the piece 15 from the top web B' constitutes the waste material.

Depending on the dimensions of the surgical drape, the piece 15 can constitute approximately 0.85 sq. meters (one square yard) of material used in constructing the surgical drape. In the embodiment in which a piece 15 is cut from both the webs A' and B', the waste can constitute approximately 1.7 sq. meters (two square yards) of material, or approximately 20% of the total material used to construct the surgical drape.

It has been found that, in some applications, it is useful for the body portion of the surgical drape to cover either to the surgical table or to the feet of the patient. However, forming the necessary fitted portions to achieve this result requires additional assembly steps and increased cost and material, which is inconsistent with the high volume/low margin nature of surgical drapes.

SUMMARY OF THE INVENTION

The present invention is directed to a surgical drape and a method of simultaneously forming a drape blank of a surgical drape in a single operation having both a screen portion and a fitted portion.

The present invention is also directed to a method of automatically constructing a series of surgical drapes with a minimum amount of waste material. Each of the surgical drapes has an elongated body portion for covering a patient with an anesthetist's screen attached at one end and a fitted portion attached at the opposite end.

In one embodiment, a first continuous web forming a body portion of a surgical drape is advanced along a first longitudinal axis to a cutting and bonding location. A second web having first and second long edges generally parallel to a second longitudinal axis is located so that the first long edge of the second web is adjacent to the cutting and bonding location. A curvilinear seam is formed between the first and second webs along a path extending into the second web. The path generally originates and terminates at the intersection of the first long side of the second web and the first and second long edges of the first continuous web, respectively. The seam is cut generally along the path so that a first portion of a second web forms a fitted portion with the body portion of a first surgical drape in the series of surgical drapes. A second portion of the second web forms a screen portion attached to the body portion of a second surgical drape in the series of surgical drapes. Consequently, little or no waste material is generated.

In an alternate embodiment, the body portion, screen portion and fitted portions may be assembled manually to form the present surgical drape. Cutting the first and second webs into the three components prior to assembly offers the same material utilization advantages as the automated method discussed above.

In the preferred embodiment, the second web, which forms a portion of the first and second surgical drapes, generally has a length greater than the width of the first web. Additionally, the step of forming a curvilinear seam and cutting the seam edge preferably occurs simultaneously. In one embodiment, the second longitudinal axis is generally perpendicular to the first longitudinal axis of the first continuous web.

The first portion of the second web can assume a variety of shapes, such as continuous or discontinuous curves, rectangles and trapezoids. In one embodiment, the first portion of the second web comprises an isosceles trapezoid arranged so that its long side is adjacent to the first long edge of the second web. The short side of the isosceles trapezoid may have a length generally corresponding to the width of a surgical table. In one embodiment, the legs or angled sides of the isosceles trapezoid define an angle of approximately 45° with respect to the first long edge. Generally, the angle will increase for wider surgical tables. In an alternate embodiment, the seam between the first and second webs defines a continuous curve.

The second web may comprise either discrete pieces of material or a continuous web which is advanced to the cutting and bonding portion with the first continuous web. In the embodiment in which the second web comprises a continuous web, a step of cutting the second web perpendicular to its longitudinal axis to form the screen portion is required. The second web may alternatively be advanced to the cutting and bonding location along the first longitudinal axis.

The first continuous web and the second web may be made from any flexible fluid resistant or substantially fluid impervious material such as non-woven materials made from wood pulp; fibers of a thermoplastic polymeric material; cellulose non-woven fibers; and combinations of these materials that may have been rendered fluid resistant or substantially fluid impervious by application of a chemical treatment. The second web preferably may be made from totally fluid impervious materials. It will be understood that the first and second webs do not need to be constructed from the same materials. The present surgical drape may either be disposable or reusable.

In an embodiment in which the first and second webs are constructed of a thermoplastic material, the seam joining the webs can be formed by a variety of thermal bonding techniques. Alternatively, a variety of other bonding methods may be used for forming the seam of the present invention, such as glues, adhesives, hot melt adhesives, double coated adhesive tapes, transfer adhesives or stitching.

The fitted portion of the finished drape may be turned partially or completely inside out to form an inverted fitted portion. The inverted fitted portion may be used to cover the end of a surgical table or for receiving a patient's feet. The size and shape of the first portion of the second web is somewhat dependent on the materials from which the first and second webs are constructed. For example, thick or resilient materials may be better suited for larger or uniformly shaped fitted portions.

A center seam may be formed in the fitted portion generally along the first longitudinal axis to form a pair of foot receiving covers. A cut along the center seam forms first and second fitted portions, which also may be turned partially or completely inside out to form first and second independent inverted foot receiving portions. One or more fenestrations may be formed in the surgical drapes.

Definitions as used in this application:

"Fenestration" is used herein to describe slits, cuts, or other openings in the body portion of a surgical drape located to facilitate the surgical procedure for which the drape will be employed, including absorbent fabric materials which are backed with an impervious plastic film.

"Thermal bonding" is used herein to describe bonding materials having a thermoplastic component using a hot bar, ultrasonic or impulse welding, either alone or in combination with pressure.

"Moisture vapor permeable" is used herein to describe materials which readily permit the passage of water vapor through the material but do not allow the passage of liquid water.

"Bond strength" means the force required to delaminate or separate a seam in the surgical drape.

"Thermoplastic" means a polymeric material having a thermoplastic component which may include polyolefins, polyesters, polyetheresters, and polyamides. Examples of suitable thermoplastic polymers include, by way of illustration only, such polyolefins as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; such polyesters as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; such polyetheresters as poly(oxyethylene)-poly(butylene terephthalate), poly(oxytrimethylene)-poly(butylene terephthalate), poly(oxytetramethylene)poly(butyleneterephthalate), poly(oxytetramethylene)-poly(ethylene terephthalate), and the like; and such polyamides as poly(6-aminocaproic acid) or poly(,-caprolactam), poly(hexamethylene adipamide), poly(hexamethylene sebacamide), poly(11-aminoundecanoic acid), and the like.

DETAILED DESCRIPTION OF THE PREFERRED EMBODIMENTS

Figure 1:
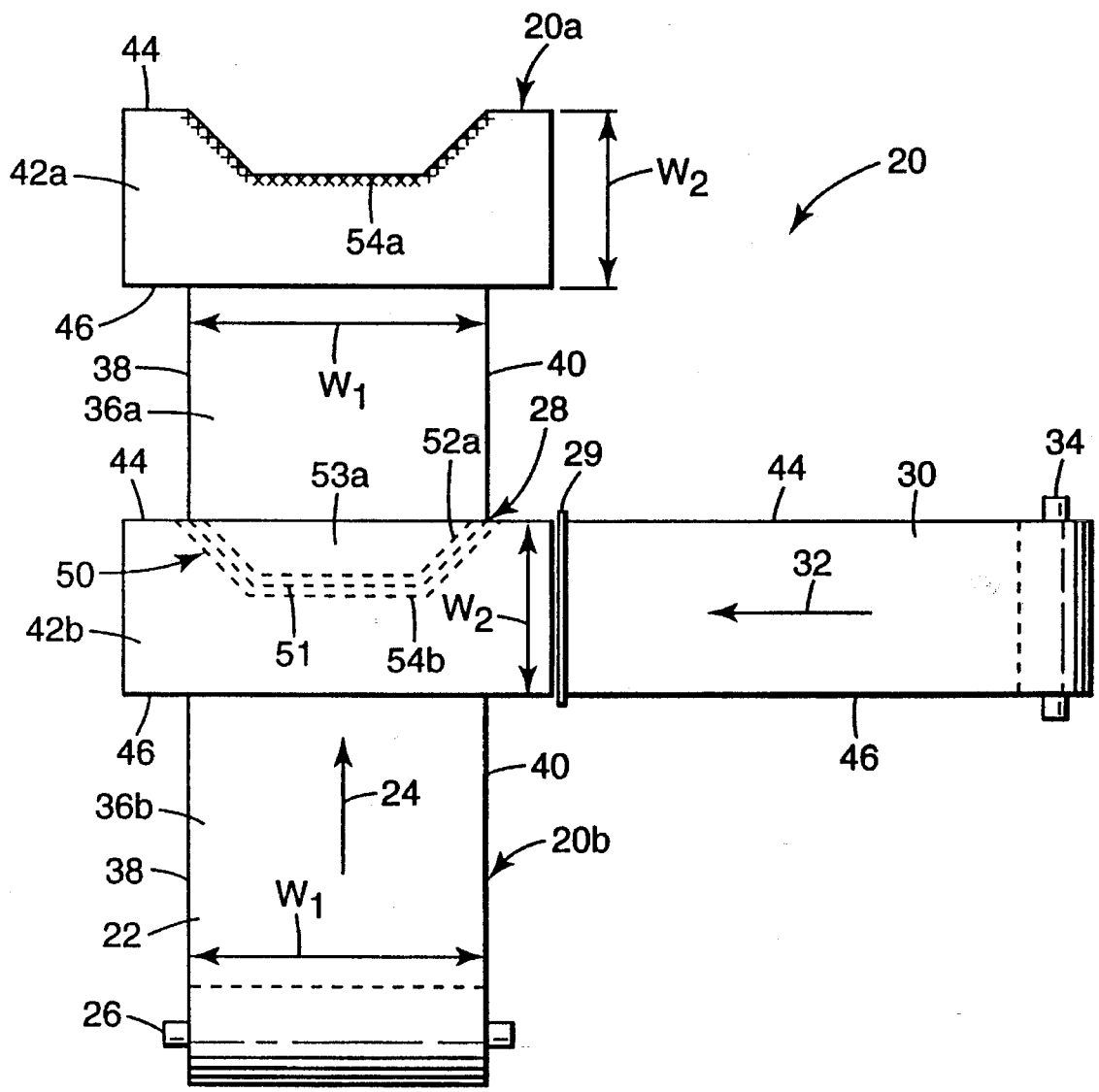
FIG. 1 is a schematic illustration of the preferred method of forming a series of surgical drapes.

FIG. 1 is a schematic illustration of a preferred method of forming a first surgical drape 20a and a second surgical drape 20b in a series of surgical drapes 20. A first continuous web 22 is fed along a first longitudinal axis 24 from a roll 26 toward a cutting and bonding location 28. A second web 30 is fed along a second longitudinal axis 32 from a roll 34 toward the cutting and bonding location 28. The second web 30 is advanced to a cutoff location 29 to form screen portions 42a–b for each of the surgical drapes 20a–b. However, it will be understood that sheet stock may be substituted for the roll 34.

In the embodiment illustrated in FIG. 1, the first longitudinal axis 24 and second longitudinal axis 32 are preferably orthogonal. The first continuous web 22 supplies the body portions 36a–bof the series of surgical drapes 20a–b. Each of the body portions 36a–bhas a first long edge 38, a second long edge 40, and a width The second web 30 supplies the screen portions 42a–b of the series of surgical drapes 20a–b. Each of the screen portions 42a–b has a first long edge 44, a second long edge 46, and a width $W_2$. The second web 30 is advanced so that the first long edge 44 of each screen portion 42a–b is adjacent to the cutting and bonding location 28.

As illustrated in FIG. 1, a seam 50 is formed between the screen portion 42b of the second web 30 and the body portion 36b of the first continuous web 22 along a path that extends into the second web 30. The seam 50 generally originates and terminates at the intersection of the first long edge 44 of the second web 30 and the first and second long edges 38, 40 of the first continuous web 22, respectively. The seam 50 forms an isosceles trapezoid on the screen portion 42b of the second web 30. However, it will be understood that a variety of seam path configurations are possible, such as continuous or discontinuous curves, rectangles or trapezoids.

As illustrated in FIG. 1, the seam 50 is severed along cut line 51. The cut line 51 separates seam 50 into a fitted portion seam 52a on the first surgical drape 20a and a drape-body seam 54b on the second surgical drape 20b. The fitted portion seam 52a attaches a fitted portion 53a of the second web 30 to the base of the body portion 36a of the first surgical drape 20a. Screen portion 42b is attached to body portion 36b of the second surgical drape 20b by the screen-body seam 54b on the opposite side of the cut line 51. Screen portion 42a is attached to a body portion 36a of the first surgical drape 20a by the screen-body seam 54a. The portion of the cut line 51 that is parallel to the first long edge 44 of the screen portion 42 preferably has a length approximately equal to the width $w_3$ of the surgical table (see FIG. 6). The fitted-portion seam 52a and the screen-body seams 54a–b preferably have a bond strength of about 17.86 kg/m (1 pound/inch) or greater.

The first continuous web and the second web may be made from any flexible fluid resistant or substantially fluid impervious material such as non-woven materials made from wood pulp; fibers of a thermoplastic polymeric material, including melt-blown polymer fibers, such as melt-blown polypropylene fibers, and including spunbond polymer fiber such as spunbond polyethylene and polypropylene fibers, and synthetic polymer fibers, such as polypropylene, polyethylene or other polyolefins, polyester, acrylic, polyamide and nylon fibers; cellulose non-woven fibers such as rayon; and combinations of these materials that may have been rendered fluid resistant or substantially fluid impervious by application of a chemical treatment. The second web preferably may be made from totally fluid impervious materials, such as plastics including polyolefins, such as polyethylene and polypropylene; and polyester; polyamide; polyurethane; polyvinyl chloride and the like. The plastics may be co-extruded and or blended to form multilayered materials.

Particularly preferred materials for use as both webs are the non-woven fabric/plastic film laminate materials commonly used in the surgical drape art, such as those disclosed in U.S. Pat. No. 4,522,203 issued to Mays on Jun. 11, 1985 and/or U.S. Pat. No. 3,809,077 issued to Hansen on Jul. 25, 1974, both of which are hereby incorporated by reference. Particularly preferred non-woven fabric/plastic film laminate materials include a layer of polyethylene film sandwiched between two layers of non-woven rayon (commercially available as "STERI-DRAPE™ Blue Fabric" from 3M Company, St. Paul, Minn.); melt-blown polypropylene fabric; and a combination of wood pulp and polyester fibers (commercially available as "ASSURE™ I, II, or III Nonwoven Fabric" from Dexter Corporation, Windsor Locks, Conn.).

Particularly preferred non-woven fabric materials are made from spunbonding or spunlacing thermoplastic polymeric fibers. Particularly preferred materials include those made from spunbonding thermoplastic polymeric fibers, wherein 100 percent of the fibers are melt blown polypropylene fibers; spunlacing thermoplastic polymeric fibers, wherein 100 percent of the fibers are polyester (commercially available as NEXUS™ 100% Polyester" from Burlington Formed Fabrics, Greensboro, N.C.); spunbonding thermoplastic polymeric fibers, wherein 100 percent of the fibers are nylon fibers, (commercially available as CEREX™ Spunbonded Nylon" from James River Corp., Simsonville, N.C.); spunbond/meltblown/spunbond laminate materials (available from Kimberly-Clark Corporation and sold under the trade name Evolution Fabric System); and spunbonding thermoplastic polymeric fibers, wherein 100 percent of the fibers are polyester (commercially available as "REEMAY™ Spunbonded Polyester" from E.I. DuPont de Nemours and Company, Wilmington, Del.) and spunlacing a combination of thermoplastic and cellulosic fibers, such as hydroentanging cellulose and polyester fibers (commercially available as "SONTARA™ Spunlaced Fabric" from E.I. DuPont de Nemours and Company) and rendering it fluid resistant or substantially fluid impervious by application of a chemical treatment.

Preferred materials may include woven or knit fabrics are made from cotton, rayon, acrylic, polyester, polyolefin, and nylon fibers and blends thereof that may have been rendered fluid resistant or substantially fluid impervious by application of a chemical treatment and/or laminated to the totally impervious materials described above. The drape as a whole may be made from a breathable nonwoven material and the area surrounding the fenestration may be made fluid impervious (e.g., by adding a layer of plastic film or by treating the nonwoven material with a coating of fluid impervious material) or fluid absorbent material (e.g., by adding a layer of absorbent material available under the trade name Drysite from Johnson and Johnson Medical, Inc.)

Alternatively preferred materials include a moisture vapor permeable microporous membranes with viral barrier capabilities, such as those disclosed in U.S. Pat. No. 4,539,256 issued to Shipman on Sep. 3, 1985 and/or U.S. Pat. No. 5,260,360 issued to Mrozinski et al on Nov. 9, 1993, both of which are hereby incorporated by reference and particularly preferred materials include microporous membranes laminated on one or more sides with the non-woven materials or plastic films described above. Webs made of thermoplastic polymeric fibers are particularly preferred since they can be heat bonded and cut simultaneously Without the use of adhesives.

For certain types of surgery, a metal layer may be interposed between layers of the webs or on one side thereof. Preferably the metal layer is a metal foil of aluminum, cerium, cobalt, copper, gold, indium, iron, lead, molybdenum, neodymium, nickel, palladium, platinum, praseiodymium, rhenium, rhodium, samarium, silver, tantalum, tin, titanium, tungsten, vanadium, zinc, and their alloys such as stainless steel.

Certain conventional additive materials may also be included in the polymer melt or topically applied to the plastic films, microporous membranes or non-woven materials. Such additives may include, for example, dyes, pigments, plasticizers, anti-blocking agents, absorbent fibers, antistatic agents, foaming agent, fluorochemical compounds, UV absorbers, antioxidants, bactericides, fungicides, ionizing radiation resistant additives, and the like.

The seams 52, 54 may be created by a variety of techniques, such as impulse or ultrasonic welding, application of a glue, adhesive, hot melt adhesive, thermal bonding, or a double coated adhesive tape or a transfer adhesive. In the preferred embodiment, the cut line 51, fitted portion seam 52 and the screen-body seam 54 are all formed simultaneously. In an embodiment in which the first and second webs are constructed of thermoplastic materials, the step of forming the curvilinear seam may include thermally bonding the first and second webs along the path. It will be understood that the body portion 36 and screen portion 42 may be formed from different materials. For example, it may be desirable to use a lower cost material for the body portion 36.

Figure 2:
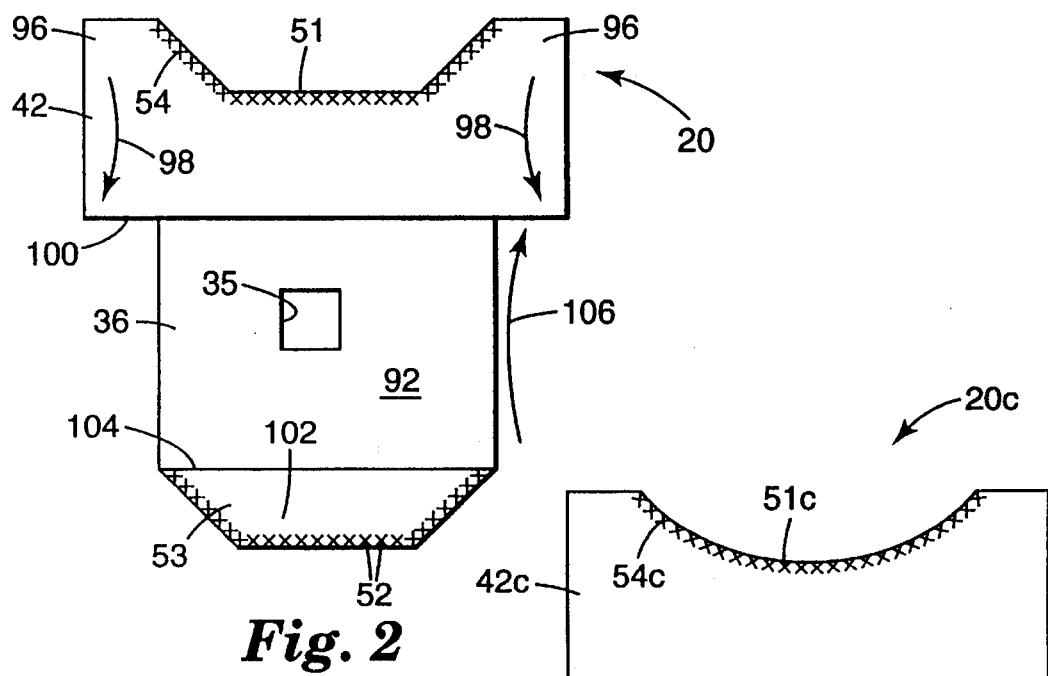
FIG. 2 illustrates a first embodiment of a finished surgical drape constructed according to the present method.

As illustrated in FIG. 2, surgical drape 20 includes a screen portion 42 attached to body portion 36 by a screen-body seam 54 along the cut line 51. The fitted portion 53 is attached to the opposite end of the body portion 36 by a fitted portion seam 52. The fitted portion 53 may be turned partially or completely inside out to form an inverted fitted portion 60, as will be discussed below. The inverted fitted portion 60 may be folded over the end of a surgical table (see FIG. 5) or used to receive the feet of a patient (see FIG. 6).

Body portion 36 may include one or more fenestrations 35 for facilitating the surgical procedure. It will be understood that reinforcing elements may be desirable at various locations on the body portion 36 or screen portion 42. For example, tubing tabs or clamping tabs may be attached to the body portion 36 proximate the fenestation 35 or at other locations. Additionally, pocket or pouch structures may be formed in the body portion 36 for receiving and containing liquids resulting from the surgical procedure.

Figure 2A:
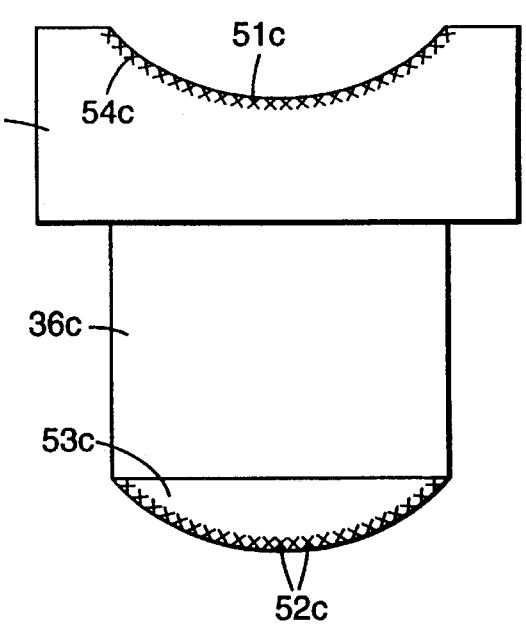
FIG. 2A illustrates an alternate embodiment of a finished surgical drape constructed according to the present method.

FIG. 2A illustrates an alternate surgical drape 20c having a screen portion 42c attached to body portion 36c by a curved screen-body seam 54c along the cut line 51c. As discussed in connection with FIG. 2, the fitted portion 53c is attached to the opposite end of the body portion 36c by a fitted portion seam 52c.

Figure 3:
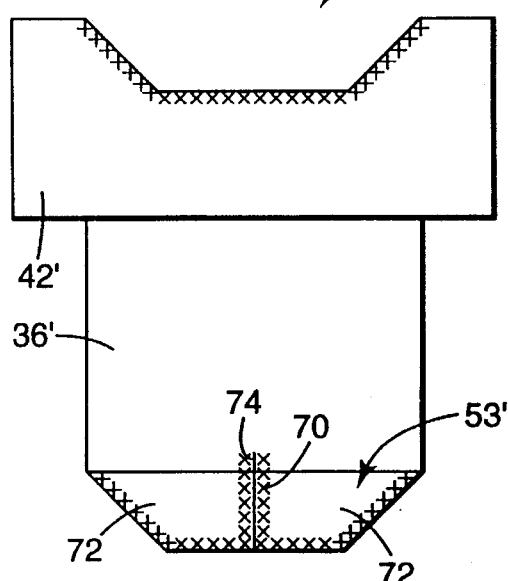
FIG. 3 is an alternate surgical drape constructed according to the present method having a pair of independent leggings.

FIG. 3 illustrates an alternate embodiment of a surgical drape 20' having a body portion 36' and a screen portion 42'. A center seam 70 is formed in the fitted portion 53' to create a pair of leggings 72 for receiving the feet of a patient (see FIG. 6). The center seam 70 preferably includes a center cut line 74 that generally bisects the center seam 70 so that the leggings 72 can be separated as needed. As discussed in connection with FIG. 2, the leggings 72 may be turned inside out to form first and second inverted foot pockets 76, 78 (see FIG. 6).

Figure 4:
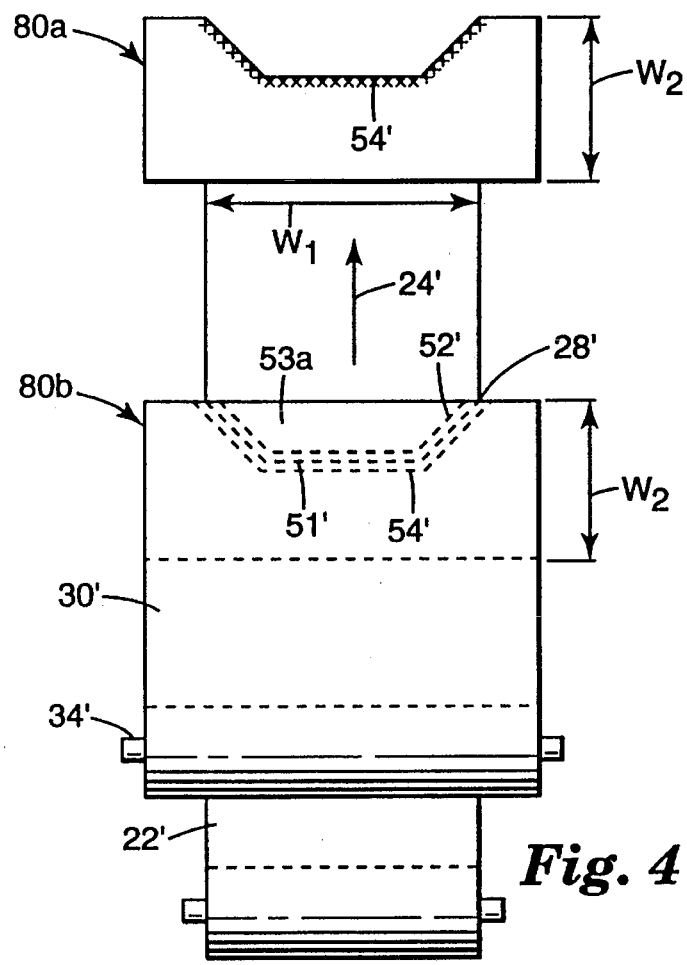
FIG. 4 is a schematic illustration of an alternate method of manufacturing a series of surgical drapes.

FIG. 4 illustrates an alternate method for constructing a series of surgical drapes 80a–b. In this alternate embodiment, the second web 30' is supplied from a roll 34' which feeds parallel to the first longitudinal axis 24' of the first continuous web 22'. The second web 30' is advanced to a cutting and bonding location 28' where a fitted portion seam 52' and a screen-body seam 54' are formed on opposite sides of a cut line 51', similar to the method disclosed in connection with FIG. 1. The disadvantage of the embodiment illustrated in FIG. 4 is that the roll stock 34' of the second web 30' is wider, and therefore generally more expensive than the roll stock 34 of the second web 30 of FIG. 1.

Figure 5:
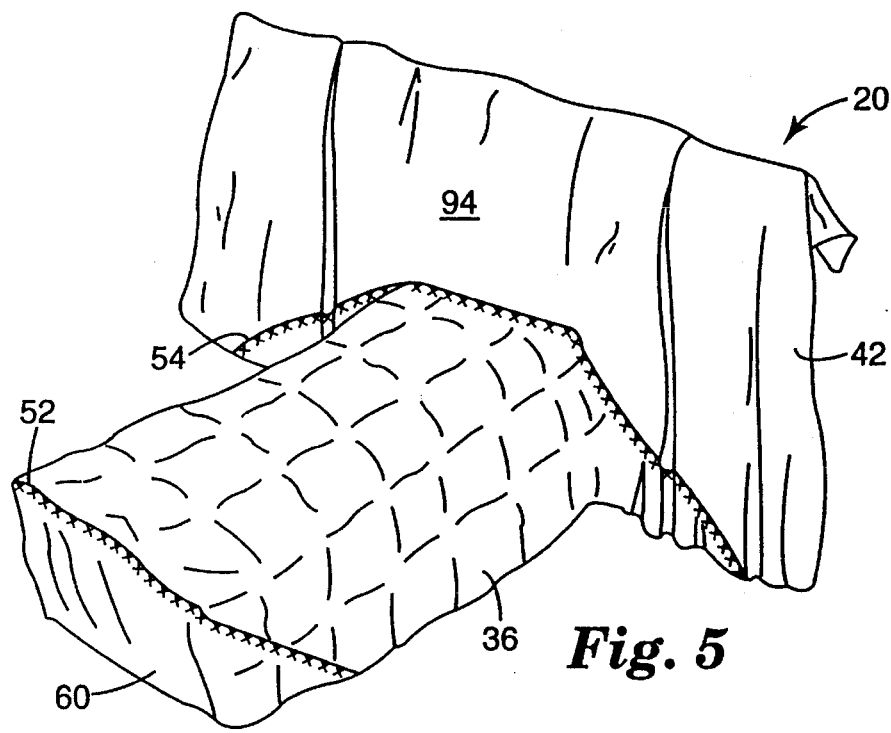
FIG. 5 is a perspective illustration of the surgical drape of FIG. 2 applied to a surgical table.
Figure 6:
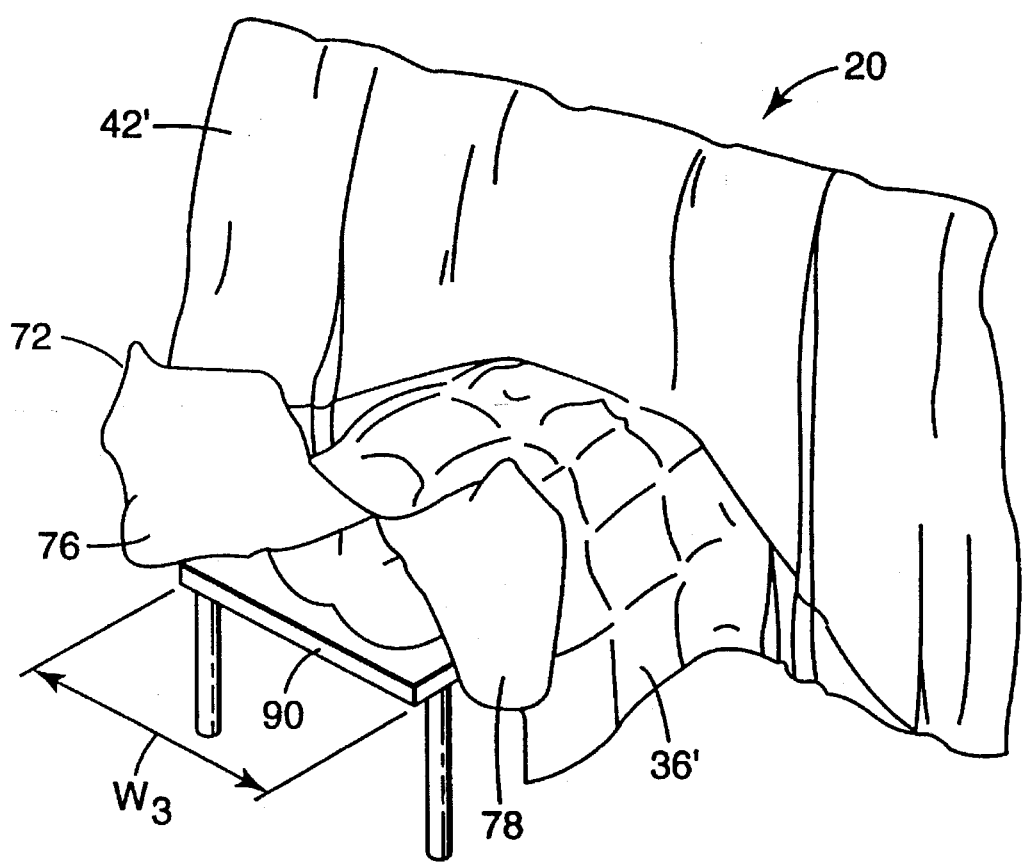
FIG. 6 is a perspective illustration of the surgical drape of FIG. 3 applied to a patient on a surgical table.

FIG. 5 illustrates application of an exemplary surgical drape 20 on a surgical table 90 (see FIG. 6). The screen portion 42 attached to the body portion 36 along a drape-body seam 54 is supported on an anesthetist's arch (not shown). The body portion 36 drapes over the surgical table 90 and extends down the sides thereof. The inverted fitted portion 60 attached to the body portion 36 along a fitted portion seam 52 extends down over the foot of the surgical table 90 to form a fitted foot drape.

FIG. 6 illustrates application of the alternate surgical drape 20' illustrated in FIG. 3 applied to a surgical table 90. The screen portion 42' is supported by an anesthetist's arch (not shown), as discussed in connection with FIG. 5. The body portion 36' drapes over the patient and extends down the sides of the surgical table 90. The leggings 72 are separated along the center cut line 74 (see FIG. 3) and turned inside out to form first and second inverted foot covers 76, 78 for receiving the feet of the patient. The first and second inverted covers 76, 78 are particularly useful as vertical leg coverings. The integral leg coverings 76, 78 formed in the surgical drape 20' are desirable in surgical drapes used in gynecological or lithotomy procedures when the patient's legs are held in an elevated position above the level of the operating table.

Turning back to FIG. 2, the present surgical drape 20 is preferably folded so that the top surface 92 of the body portion 36 and front surface 94 (see FIG. 5) of the screen portion 42 do not contact the patient or any other source of contamination during the unfolding process. The lower side edges 96 of the screen portion 42 are folded along a path 98 toward the fitted portion 53. The folded screen portion 42 is then fan folded so that the edge 100 is presented to the surgical staff for gripping during unfolding. The fitted portion 53 is invert folded so that the sterile sides 102 (top and bottom of the fitted portion 53 ) are at the interior of the folded fitted portion 53. The folded fitted portion and body portion 36 are then fan folded along a path 106 so that the top edge 104 of the fitted portion 53 is presented for gripping by the surgical staff during unfolding.

The folded surgical drape article is placed on the patient proximate the chest area. The screen portion 42 is pulled upward and attached to the anesthetist's arch by gripping the edge 100. The edge 104 on the fitted portion 53 is pulled toward the patient's feet and either folded over the end of the surgical table (see FIG. 5) or the patient's feet (see FIG. 6). Consequently, the top surface 92 of the body portion 36 and the from surface 94 of the screen portion 42 remain aseptic during the unfolding process.

It will be understood that the exemplary embodiments in no way limit the scope of the invention. Other modifications of the invention will be apparent to those skilled in the art in view of the foregoing descriptions. These descriptions are intended to provide specific examples of embodiments which clearly disclose the invention. Accordingly, the invention is not limited to the described embodiments or to the use of specific elements, dimensions, materials or configurations contained therein. All alternative modifications and variations of the present invention which fall within the spirit and broad scope of the appended claims are covered.

What is claimed is:

1. A method for making a series of surgical drapes comprising the steps of:

advancing a first continuous web forming a body portion of a surgical drape along a first longitudinal axis to a cutting and bonding location, the first continuous web having a first width perpendicular to the first longitudinal axis and first and second long edges generally parallel to the first longitudinal axis;

locating a second web having first and second long edges generally parallel to a second longitudinal axis so that the first long edge of the second web is adjacent to the cutting and bonding location and the second longitudinal axis is generally perpendicular to the first longitudinal axis;

forming a curvilinear seam between the first and second webs along a path extending into the second web, the path generally originating and terminating proximate the intersections of the first long edge of the second web and the first and second long edges of the first continuous web, respectively; and cutting the first continuous web and second web generally along the path so that a first portion of the second web forms a fitted portion on the body portion of a first surgical drape and a second portion of the second web forms a screen portion attached to the body portion of a second surgical drape in the series of surgical drapes.

2. The method of claim 1 wherein the first portion of the second web has a shape comprising an isosceles trapezoid having two sides of equal length, a short side, and a long side adjacent to the first long edge of the second web.

3. The method of claim 2 wherein the short sides define an angle of approximately 45 degrees with the first long edge of the second web.

4. The method of claim 1 wherein the step of locating the second web adjacent to the cutting and bonding location comprises advancing the second web along the first longitudinal axis.

5. The method of claim 1 wherein the path comprises a continuous curve.

6. The method of claim 1 wherein the second web comprises a continuous second web and the step of advancing the second web further comprises the step of cutting the second web perpendicular to the second longitudinal axis to form the screen portion.

7. The method of claim 1 wherein the long edges of the second web have a length greater than the width of the first web.

8. The method of claim 1 wherein the step of forming a curvilinear seam and cutting the seam occurs generally simultaneously.

9. The method of claim 1 wherein the first continuous web is oriented below the second web.

10. The method of claim 1 wherein the first continuous web comprises a moisture vapor permeable microporous membrane with viral barrier properties.

11. The method of claim 1 wherein the first and second webs comprise polymeric materials and the step of forming a curvilinear seam comprises thermally bonding the first and second webs.

12. The method of claim 1 wherein the step of forming a curvilinear seam comprises interposing an adhesive between the first and second webs along the path.

13. The method of claim 1 further including the step of at least partially turning the fitted portion on the body portion inside-out to form an inverted fitted portion.

14. The method of claim 13 further including the step of coverting the end of the surgical table with the inverted fitted portion.

15. The method of claim 13 further including the step of coveting a patient's feet with the inverted fitted portion.

16. The method of claim 1 further including the step of forming a center seam in the fitted portion of the body portion generally along the first longitudinal axis to form a pair of foot receiving covers.

17. The method of claim 16 further including the steps of:
cutting the center seam in the fitted portion to form first and second fitted portions; and
turning the first and second fitted portions inside-out to form first and second inverted foot receiving portions.

18. The method of claim 1 further including the step of forming at least one fenestration in the body portion of the surgical drape.

19. The method of claim 1 wherein the first continuous web and second web comprise different materials.

20. A surgical drape preparable by the process of claim 1.

21. A method for making a surgical drape comprising the steps of:
providing a first web forming a body portion of a surgical drape, the first web having a first width perpendicular to a first longitudinal axis, first and second long edges generally parallel to the first longitudinal axis and first and second short edges joining the first and second long edges;
locating the first short edge of the first web at a cutting and bonding location;
locating a second web having first and second long edges generally parallel to a second longitudinal axis so that the first long edge of the second web is adjacent to the cutting and bonding location and the second longitudinal axis is generally perpendicular to the first longitudinal axis;
forming a first curvilinear seam between the first and second webs along a path extending into the second web, the path generally originating and terminating proximate the intersections of the first long edge of the second web and the first and second long edges of the first web, respectively;
cutting the first web and second web generally along the path so that a first portion of the second web forms a screen portion attached to the body portion of the surgical drape; and
attaching a second portion of the second web proximate the second short edge of the first web to form a fitted portion on the body portion of a the surgical drape.

22. The method of claim 21 wherein the step of providing a first web comprises providing a first web with a first short edge having a shape corresponding to the path.

23. A surgical drape preparable by the process of claim 20.

* * * * *